(12) United States Patent
Arjunan et al.

(10) Patent No.: US 8,334,385 B2
(45) Date of Patent: Dec. 18, 2012

(54) PROCESS FOR THE PREPARATION OF R-SITAGLIPTIN AND ITS PHARMACEUTICALLY ACCEPTABLE SALTS THEREOF

(75) Inventors: Sankar Arjunan, Mumbai (IN); Mahendra Raghunath Patil, Mumbai (IN); Mubeen Ahmed Khan, Mumbai (IN)

(73) Assignee: Glenmark Generics Limited, Sawant Marg, Chakala, Andheri (East), Mumbai ( * ) Notice: Subject to any disclaimer, the term of this patent is extended or adjusted under 35 U.S.C. 154(b) by 185 days.

(21) Appl. No.: 12/740,693

(22) PCT Filed: Oct. 27, 2008

(86) PCT No.: PCT/IN2008/000707
§ 371 (c)(1),
(2), (4) Date: Apr. 30, 2010

(87) PCT Pub. No.: WO2009/084024
PCT Pub. Date: Jul. 9, 2009

(65) Prior Publication Data
US 2010/0317856 A1  Dec. 16, 2010

(30) Foreign Application Priority Data
Nov. 2, 2007  (IN) .......... 2190/MUM/2007

(51) Int. Cl.
*C07D 471/00* (2006.01)

(52) U.S. Cl. ....................... 544/350
(58) Field of Classification Search ........ 544/350
See application file for complete search history.

(56) References Cited

U.S. PATENT DOCUMENTS

| 6,699,871 B2 | 3/2004 | Edmondson et al. |
| 7,326,708 B2 | 2/2008 | Cypes et al. |
| 2006/0194977 A1 | 8/2006 | Xiao et al. |
| 2008/0058522 A1 | 3/2008 | Xiao et al. |

FOREIGN PATENT DOCUMENTS

| WO | 2004085661 A2 | 7/2004 |
| WO | 2004087650 A2 | 10/2004 |
| WO | 2005003135 A1 | 1/2005 |
| WO | 2006081151 A1 | 3/2006 |

*Primary Examiner* — Douglas M Willis
(74) *Attorney, Agent, or Firm* — MLouisa Lao

(57) ABSTRACT

The present invention provides processes for the preparation of R-sitagliptin (as shown) and its pharmaceutically acceptable salts thereof.

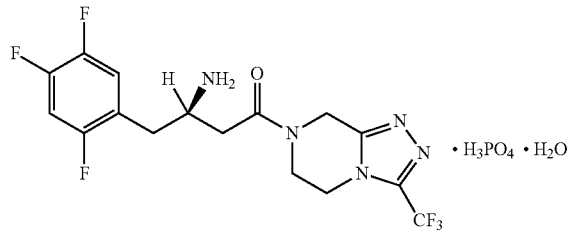

2 Claims, 4 Drawing Sheets

PROCESS FOR THE PREPARATION OF R-SITAGLIPTIN AND ITS PHARMACEUTICALLY ACCEPTABLE SALTS THEREOF

PRIORITY

This application is a National Stage Application of PCT/IN2008/000707 filed on Oct. 27, 2008; which claims the benefit of Indian Provisional Application No. 2190/MUM/2007, filed on 2 Nov. 2007, and entitled "A PROCESS FOR THE PREPARATION OF R-SITAGLIPTIN AND ITS PHARMACEUTICALLY ACCEPTABLE SALTS THEREOF", the contents of which are incorporated by reference herein.

BACKGROUND OF THE INVENTION

1. Technical Field

The present invention relates to a novel process for the preparation of R-sitagliptin and its pharmaceutical acceptable salts thereof. The present invention also provides structurally novel intermediates useful in the disclosed process, a pharmaceutical composition and a method of treating Type-2-diabetes.

2. Description of the Related Art

R-sitagliptin is commonly available as sitagliptin phosphate, 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine phosphate (1:1) monohydrate, and has the following structural formula:

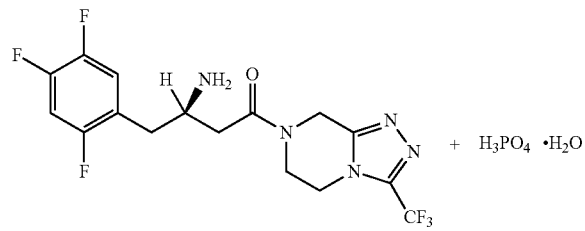

Sitagliptin phosphate is an orally administered dipeptidyl peptidase-4 (DPP-4) inhibitor. Sitagliptin has been developed for the treatment of Type-2-diabetes and is available in the market under the brand name JANUVIA® as tablets in the dosage strengths of 25, 50, or 100 mg equivalent base.

International Patent Publication WO2004087650 describes a process for the preparation of sitagliptin via benzyloxy protected tetrazolylpyrazine intermediate.

International Patent Publication WO2004085661 describes a process for the preparation of enantiomerically enriched sitagliptin via (S)-phenylglycine amide protected tetrazolyl pyrazine intermediate.

US PG Publication US20080058522 describes a process generically for the preparation of sitagliptin and its pharmaceutically acceptable salts using specific chiral bisphosphine ligands.

International Patent Publication WO2006081151 describes a process generically for the preparation of sitagliptin and its pharmaceutically acceptable salts using rhodium metal precursor complexed to a ferrocenyl diphosphine ligand.

US PG Publication US20060194977 describes a process for the preparation of Enantiomerically enriched sitagliptin using specific chiral ferrocenyl diphosphine ligands.

U.S. Pat. No. 6,699,871 describes various DPP-4 inhibitors including sitagliptin and their pharmaceutically acceptable salts, a pharmaceutical composition and method of treatment and a process for the preparation of sitagliptin hydrochloride as follows:

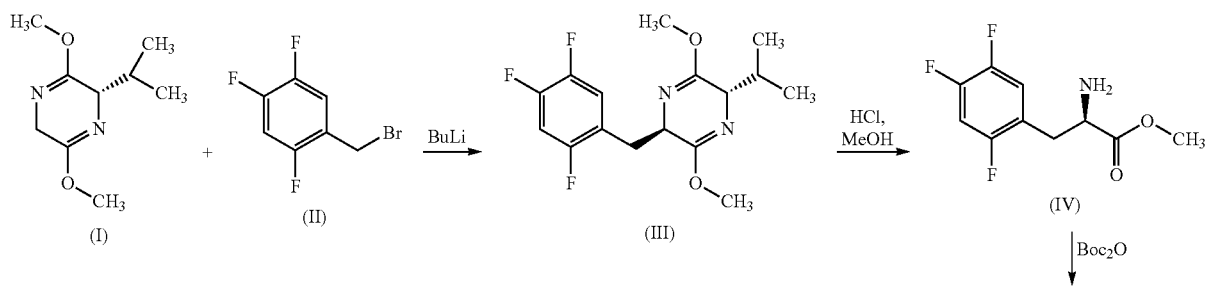

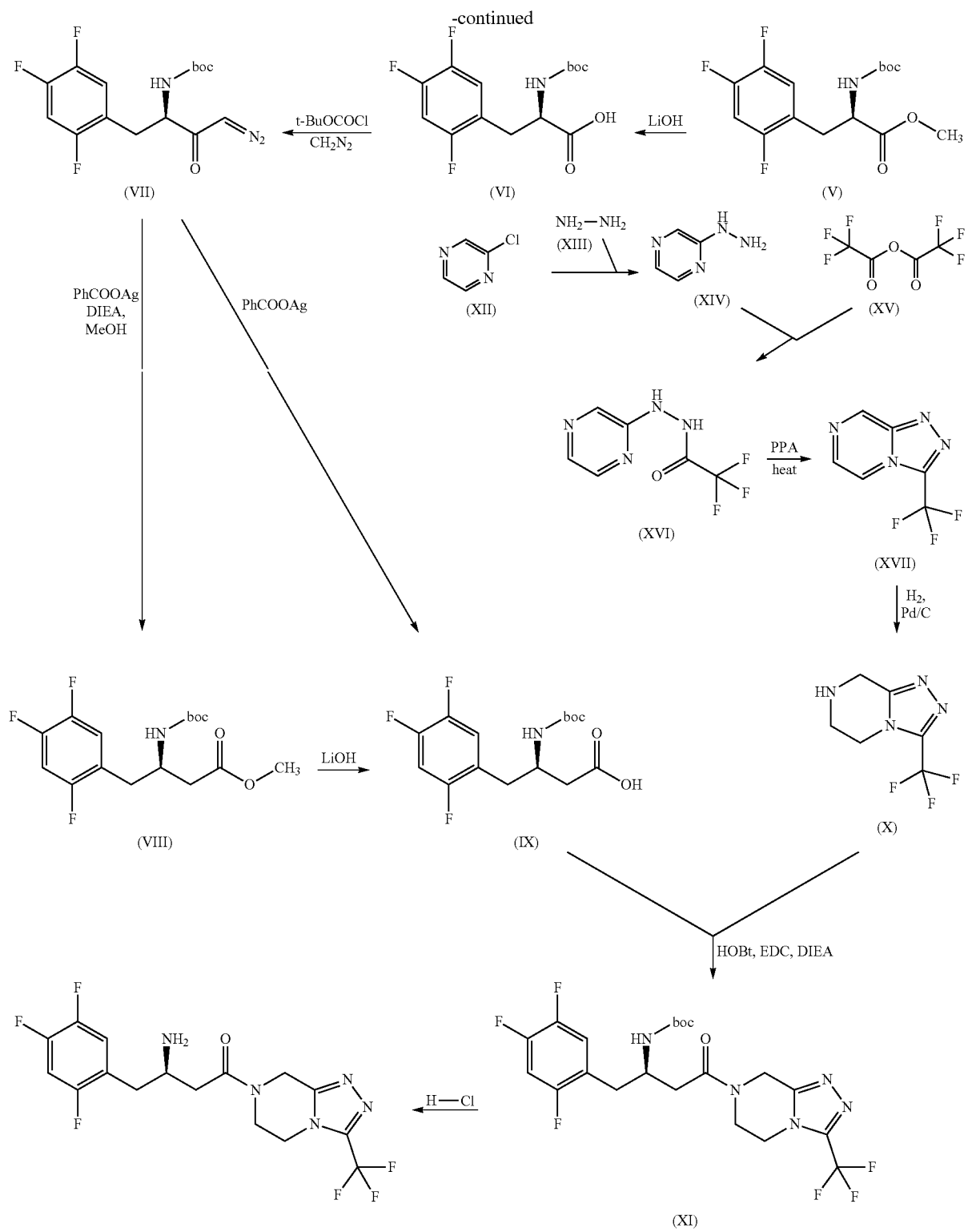

The aforementioned processes involve reactions that use specific chiral ligands or a stereo specific/stereoselective reduction process with specific stereoselective reducing agents, which are expensive and may not be commercially available, which may subsequently render the processes unsuitable on commercial scale.

Hence, there is a need for an improved process for the preparation of R-sitagliptin or its pharmaceutically acceptable salts which alleviates the problems associated with aforementioned processes as referred above.

The process of the present invention provides a process which is simple, ecofriendly, inexpensive, reproducible, robust and well suited on commercial scale.

SUMMARY OF THE INVENTION

The present invention relates to a process for the preparation of R-sitagliptin and its pharmaceutically acceptable salts thereof.

In one aspect, the present invention relates to a process for preparing R-sitagliptin of formula [Ia]

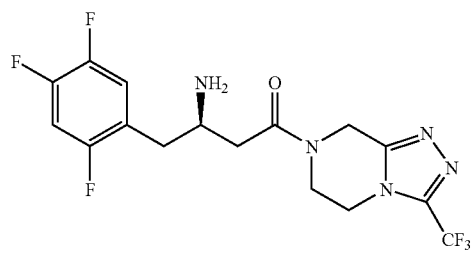

[Ia]

or a pharmaceutically acceptable salt thereof, comprising:
(a) resolving racemic sitagliptin of formula III

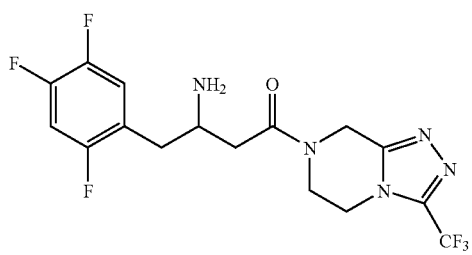

(III)

with a chiral acid to obtain a salt of the chiral acid and R-sitagliptin of formula II

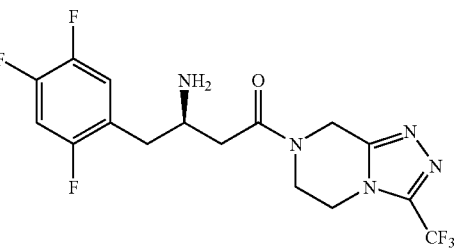

(II)

·X where X is the chiral acid; and
b) converting the salt of the chiral acid and R-sitagliptin to R-sitagliptin of Formula [Ia] or a pharmaceutically acceptable salt thereof.

In a second aspect, the present invention relates to a process for the preparation of racemic sitagliptin of formula [III] comprising:

a) reduction of 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine compound of Formula [IV]

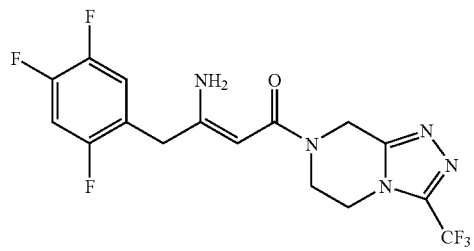

[IV]

with a reducing agent in the presence of organic solvent to give the racemic sitagliptin compound of Formula III.

In a third aspect, the present invention relates to an alternate process for the preparation of racemic sitagliptin of formula [III] comprising:
a) reaction of 3-oxime-1-[3-(trifluoromethyl)-5,6,7,8-tetrahydro[1,2,4]triazolo[4,3-a]pyrazin-7-yl]-4-(2,4,5-trifluorophenyl)butan-1-one compound of Formula [IVa]

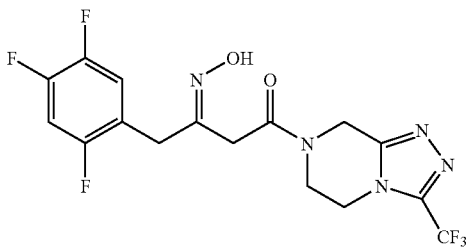

[IVa]

with a reducing agent in an organic solvent.

In a fourth aspect, the present invention relates to a to a process for preparing R-sitagliptin of formula [Ia]

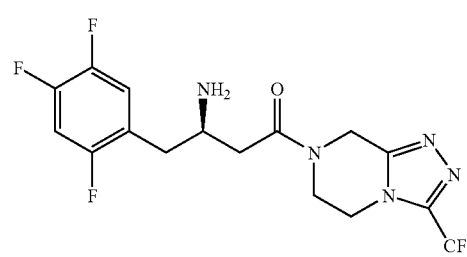

[Ia]

comprising:
a) chiral reduction of compound 3-oxime-1-[3-(trifluoromethyl)-5,6,7,8-tetrahydro[1,2,4]triazolo[4,3-a]pyrazin-7-yl]-4-(2,4,5-trifluorophenyl)butan-1-one of Formula [IVa]

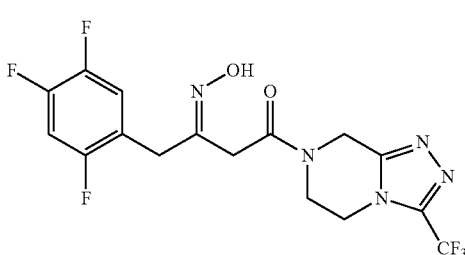

[IVa]

with a chiral reducing agent in the presence of an organic solvent.

In a fifth aspect, the present invention relates to a process for the preparation of 3-oxime-1-[3-(trifluoromethyl)-5,6,7,8-tetrahydro[1,2,4]triazolo[4,3-a]pyrazin-7-yl]-4-(2,4,5-trifluorophenyl)butan-1-one of Formula [IVa]

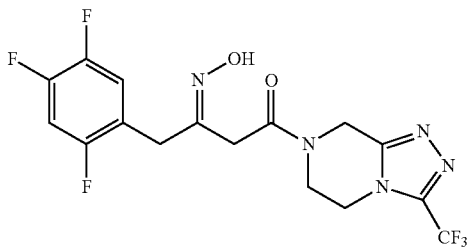

comprising:
a) reaction of 4-(2,4,5-trifluorophenyl)-3-oximebutanoic acid compound of Formula [VIIa]

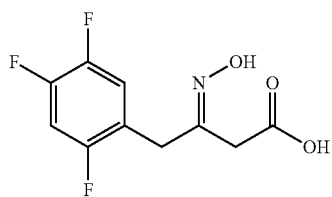

with 3-(trifluoromethyl)-5,6,7,8-tetrahydro[1,2,4]triazolo[4,3-a]pyrazine compound of formula [VI] or salt thereof,

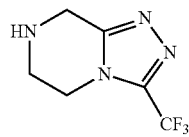

in the presence of a coupling reagent and an organic solvent.

In a sixth aspect, the present invention provides R-sitagliptin or its pharmaceutically acceptable salt thereof having less than 0.15% by weight of the corresponding (S)-enantiomer by chiral HPLC.

In a seventh aspect, the present invention provides R-sitagliptin dibenzyl-L-tartrate of formula II

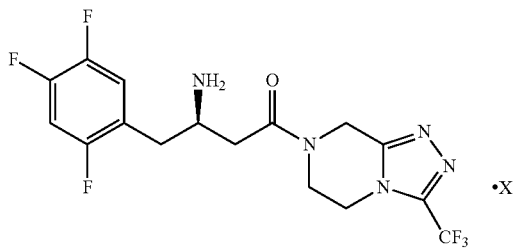

where X is dibenzyl-L-tartaric acid.

In an eighth aspect, the present invention provides R-sitagliptin dibenzyl-L-tartrate of formula II obtained by the process of the present invention having an X-ray powder diffraction (XRPD) pattern with reflections at about: 6.5, 7.4, 10.9, 12.8, 14.9, 17.4, 17.9, 19.2, 21.5, 22.4, and 23.7±0.2 degrees 2 theta.

In a ninth aspect, the present invention provides R-sitagliptin dibenzyl-L-tartrate of formula II obtained by the process of present invention having an XRPD pattern which is substantially in accordance with FIG. 1.

In a tenth aspect, the present invention provides R-sitagliptin dibenzyl-L-tartrate of formula II obtained by the process of present invention having a differential scanning calorimetry (DSC) thermogram with sharp endotherm at about 176.73° C. with onset at about 171.49° C. and endset at about 176.73° C.

In an eleventh aspect, the present invention provides R-sitagliptin dibenzyl-L-tartrate of formula II obtained by the process of the present invention having a DSC thermogram which is substantially in accordance with FIG. 2.

In a twelfth aspect, the present invention provides R-sitagliptin of formula Ia obtained by the process of the present invention having an X-ray powder diffraction (XRPD) pattern with reflections at about: 7.3, 17.6, 18.8, 21.2, 21.5, 22.4, 24.1, 24.4, 24.7, 27.0, and 28.7±0.2 degrees 2 theta.

In a thirteenth aspect, the present invention provides R-sitagliptin of formula Ia obtained by the process of the present invention having an XRPD which is substantially in accordance with FIG. 3.

In a fourteenth aspect, the present invention provides R-sitagliptin of formula Ia obtained by the process of the present invention is having a differential scanning calorimetry (DSC) thermogram with sharp endotherm at about 117.66° C. with onset at about 116.37° C. and endset at about 119.58° C.

In a fifteenth aspect, the present invention provides R-sitagliptin of formula Ia obtained by the process of the present invention having a DSC thermogram which is substantially in accordance with FIG. 4.

In a sixteenth aspect, the present invention provides a pharmaceutical composition comprising sitagliptin or its pharmaceutically acceptable salts obtained by the processes of the present invention and at least a pharmaceutically acceptable carrier.

DETAILED DESCRIPTION OF THE INVENTION

Figure 1:
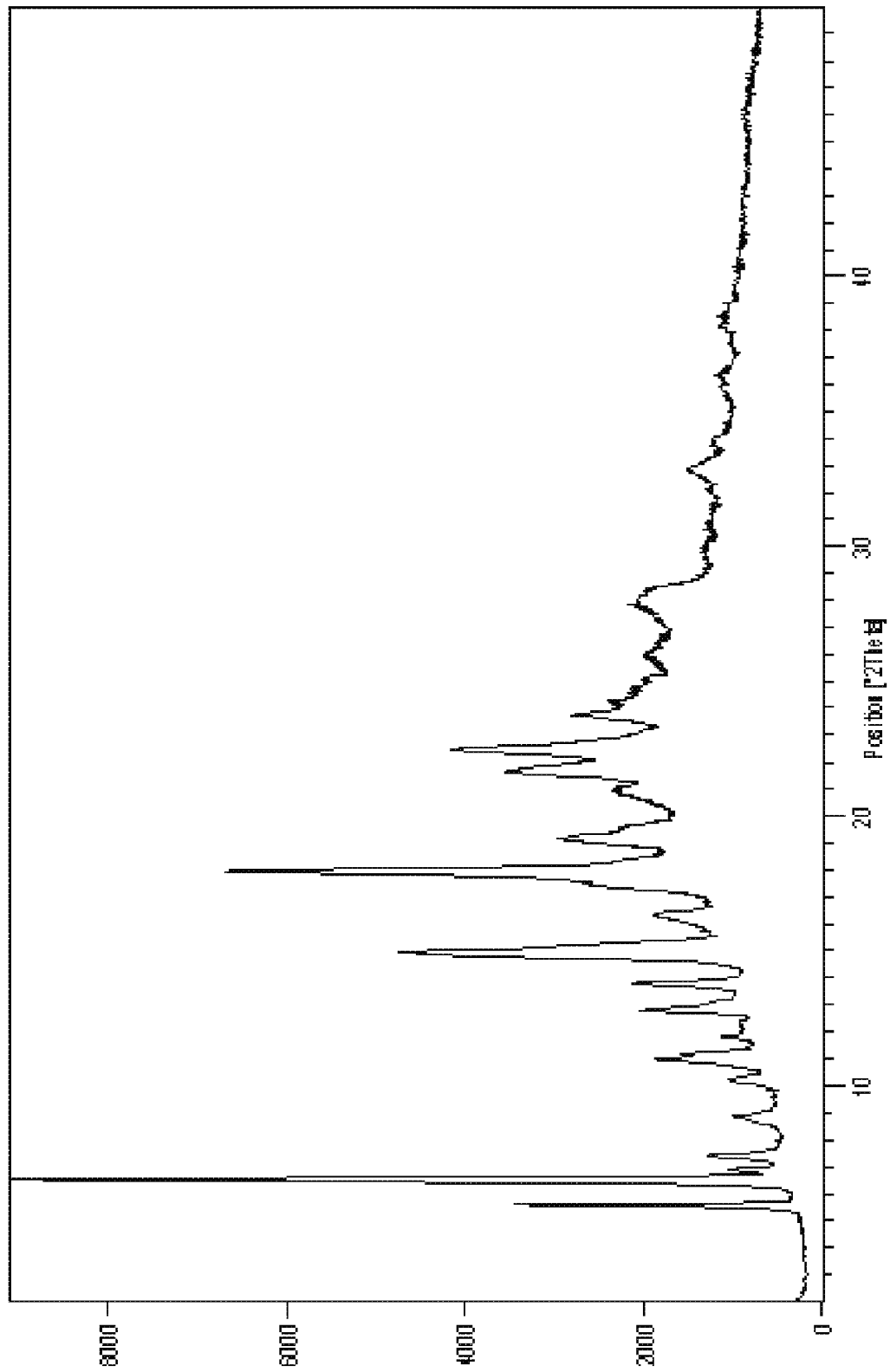
FIG. 1: Shows a powder X-ray diffraction pattern of R-sitagliptin dibenzyl-L-tartrate of Formula II as prepared by example 5c.

The present invention provides a process for preparing R-sitagliptin of formula [Ia]

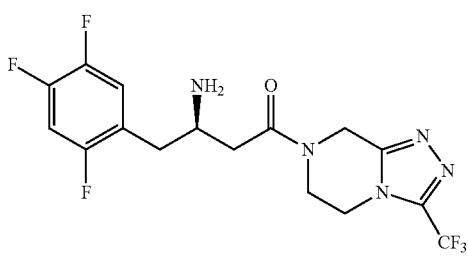

or a pharmaceutically acceptable salt thereof, comprising:
(a) resolving racemic sitagliptin of formula III

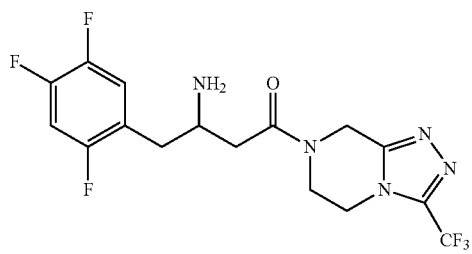

with a chiral acid to obtain a salt of the chiral acid and R-sitagliptin of formula II,

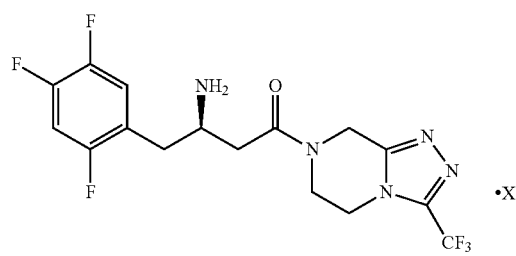

where X is chiral acid, and b) converting the salt of the chiral acid and R-sitagliptin to R-sitagliptin of Formula [Ia] or a pharmaceutically acceptable salt thereof.

The chiral acid that can be used for resolution of racemic sitagliptin is selected from the group of S-(+) mandelic acid, R-(−) mandelic acid, L-(+) tartaric acid, D-(−) tartaric acid, (−)-dibenzoyl-L-tartaric acid, (−)-dibenzoyl-L-tartaric acid monohydrate, (+)-dibenzoyl-D-tartaric acid, (+)-dibenzoyl-D-tartaric acid monohydrate, (+)-dipara-toluoyl-D-tartaric acid, (+)-dipara-toluoyl-D-tartaric acid monohydrate, (−)-dipara-toluoyl-D-tartaric acid, (−)-dipara-toluoyl-D-tartaric acid monohydrate, (1R)-(−)-10-camphorsulfonic acid, and (1S)-(+)-10-camphorsulfonic acid. Preferably the chiral acid used is (−)-dibenzoyl-L-tartaric acid.

The organic solvent that can be used is selected from the group of alcohols such as methanol, ethanol, isopropyl alcohol and the like; ketones such as acetone, ethyl methyl ketone, methyl isobutyl ketone and the like; nitriles such as acetonitrile, propionitrile and mixtures thereof or their aqueous mixtures. Preferably the solvent used is methanol.

The resolution process can be carried out at temperature range of about 0° C. to about 100° C. or reflux temperatures of the solvents used. Preferably from about 20° C. to about 70° C.

The molar equivalents of chiral acid used can be from about 0.5 to about 10 moles per moles of the racemic sitagliptin of formula III. Preferably 1:1 ratio of chiral acid and racemic sitagliptin is used.

The base that can be used is selected from the group of inorganic bases such as sodium hydroxide, potassium hydroxide, sodium carbonate, potassium carbonate, sodium bicarbonate, potassium bicarbonate, sodium methoxide, potassium methoxide and the like; organic bases such as liquid ammonia, triethylamine, diisopropylethylamine, pyridine and the like; aqueous or alcoholic mixtures thereof. Preferably aqueous sodium hydroxide.

The molar equivalents of base used can be from about 0.5 to about 10 moles per mole of the racemic sitagliptin of formula III. Preferably 1:1 ratio of base and racemic sitagliptin is used.

The present invention provides a process for the preparation of racemic sitagliptin of formula [III] comprising:

a) reducing 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine compound of Formula [IV]

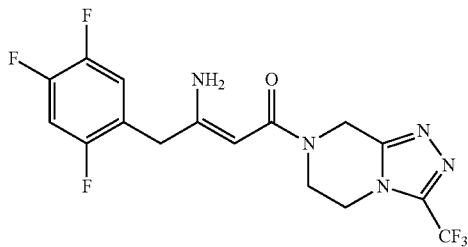

with a reducing agent in the presence of organic solvent to give the racemic sitagliptin compound of Formula III.

The reducing agents that can be used is selected from the group Raney nickel, palladium carbon, platinum, platinum dioxide, sodium borohydride, sodium triacetoxy borohydride, sodium cyanoborohydride, lithium aluminium hydride (LAH), diisobutylaluminium hydride (DIBAL-H), sodium bis(2-methoxyethoxy)aluminium hydride, tributyltin hydride, triethylsilane and the like. Preferably the reducing agent used is sodium cyanoborohydride.

The organic solvent that can be used is selected from the group of alcohols such as methanol, ethanol, isopropyl alcohol and the like; ketones such as acetone, ethyl methyl ketone, methyl isobutyl ketone and the like; nitriles such as acetonitrile, propionitrile and mixtures thereof or their aqueous mixtures. Preferably the solvent used is methanol.

The resolution process can be carried out at temperature range of about 0° C. to about 100° C. or reflux temperatures of the solvents used, preferably from about 20° C. to about 70° C.

The molar equivalents of reducing agent used can be from about 0.25 to about 10 moles per mole of racemic sitagliptin of formula III, preferably 1:1 ratio of reducing agent and racemic sitagliptin is being used.

The present invention further provides an alternate process for the preparation of racemic sitagliptin of formula [III] comprising:

a) reaction of 3-oxime-1-[3-(trifluoromethyl)-5,6,7,8-tetrahydro[1,2,4]triazolo[4,3-a]pyrazin-7-yl]-4-(2,4,5-trifluorophenyl)butan-1-one compound of Formula [IVa]

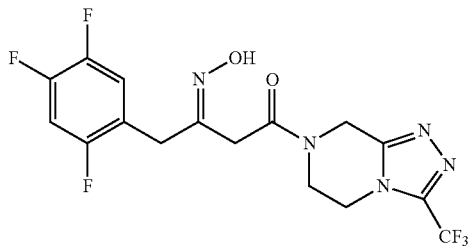

[IVa]

with a reducing agent in an organic solvent.

The reducing agents that can be used is selected from the group of Raney nickel, palladium carbon, platinum, platinum dioxide, sodium borohydride, sodium triacetoxy borohydride, sodium cyanoborohydride, lithium aluminium hydride (LAH), diisobutylaluminium hydride (DIBAL-H), sodium bis(2-methoxyethoxy)aluminium hydride, tributyltin hydride, triethylsilane and the like. Preferably the reducing agent used is palladium carbon.

The organic solvent that can be used is selected from the group of alcohols such as methanol, ethanol, isopropyl alcohol and the like; ketones such as acetone, ethyl methyl ketone, methyl isobutyl ketone and the like; nitriles such as acetonitrile, propionitrile and mixtures thereof or their aqueous mixtures. Preferably the solvent used is methanol.

The resolution process can be carried out at temperature range of about 20° C. to about 100° C. or reflux temperatures of the solvents used, preferably from about 20° C. to about 70° C.

The molar equivalents of reducing agent used can be from about 0.25 to about 10 moles per mole of the racemic sitagliptin of formula III, preferably 1:1 ratio of reducing agent and racemic sitagliptin is being used.

The present invention also provides an alternate process for preparing R-sitagliptin of formula [Ia]

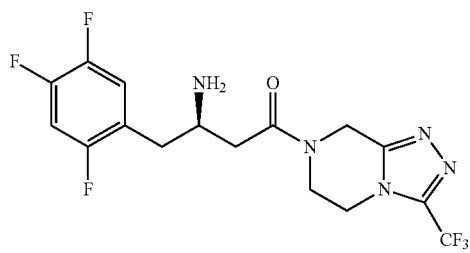

[Ia]

comprising:

a) chiral reduction of compound 3-oxime-1-[3-(trifluoromethyl)-5,6,7,8-tetrahydro[1,2,4]triazolo[4,3-a]pyrazin-7-yl]-4-(2,4,5-trifluorophenyl)butan-1-one of Formula [IVa]

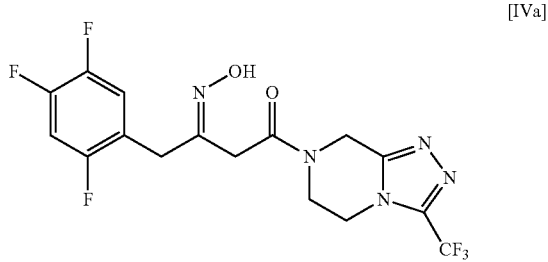

[IVa]

with a chiral reducing agent in the presence of an organic solvent.

The chiral reducing agents that can be used is selected from the group of Borne-THF complex with chiral Auxiliaries of ephedrine derivatives such as L-(−)-norephedrine, (1R,2R)-(−)-pseudoephedrinepropionamide (S)-1-methyl-3,3-diphenyl-tetrahydro-pyrrolo[1,2c][1,3,2]oxazaborole, and (S)-(−)-4-isopropyl-5,5-diphenyl-2-oxazolidinone and the like, preferably L-(−)-norephedrine.

The organic solvent that can be used is selected from the group of alcohols such as methanol, ethanol, isopropyl alcohol and the like; ketones such as acetone, ethyl methyl ketone, methyl isobutyl ketone and the like; nitriles such as acetonitrile, propionitrile and mixtures thereof or their aqueous mixtures. Preferably the solvent used is methanol.

The reduction process can be carried out at temperature range of about 30° C. to about 100° C. or reflux temperatures of the solvents used, preferably from about 60° C. to about 70° C.

The molar equivalents of chiral reducing agent used can be from about 0.25 to about 10 moles per mole of the compound of formula IVa, preferably 1:1 ratio of reducing agent and compound of formula IVa is being used.

In embodiment of the present invention, there is provided a process for the preparation of 3-oxime-1-[3-(trifluoromethyl)-5,6,7,8-tetrahydro[1,2,4]triazolo[4,3-a]pyrazin-7-yl]-4-(2,4,5-trifluorophenyl)butan-1-one of Formula [IVa]

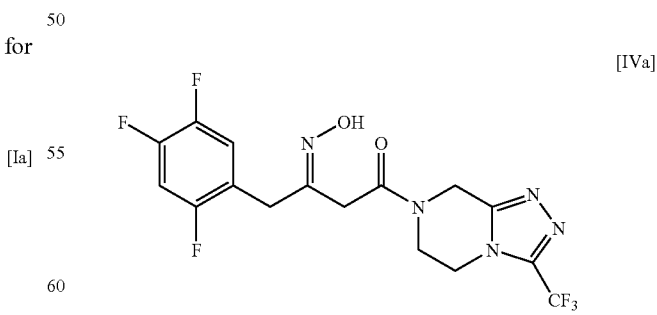

[IVa]

comprising:

a) reaction of 4-(2,4,5-trifluorophenyl)-3-oximebutanoic acid compound of Formula [VIIa]

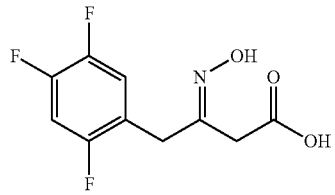

[VIIa]

with 3-(trifluoromethyl)-5,6,7,8-tetrahydro[1,2,4]triazolo[4,3-a]pyrazine compound of formula [VI] or salt thereof,

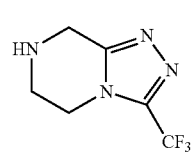

[VI]

in the presence of a coupling reagent and an organic solvent.

The coupling agent that can be used is selected from the group of benzotriazole-1-yl-oxy-tris(dimethylamino)phosphoniumhexafluoro-phosphate (BOP),N,N'-dicyclohexyl-carbodiimide (DCC), 1-hydroxibenzotriazol anhydrous(H-OBt), N-(3-dimethylaminopropyl)-N-ethylcarbodiimide (EDC) and the like. Preferably the coupling agent used is 1-hydroxibenzotriazol anhydrous (HOBt).

The organic solvent that can be used is selected from the group of ethers such as diethyl ether, diisopropyl ether, tetrahydrofuran and the like; halogenated solvents such as methylene chloride, ethylene dichloride, chloroform and the like; alcohols such as methanol, ethanol, isopropyl alcohol and the like; hydrocarbon solvents such as n-hexane, n-heptane, cyclohexane, toluene and the like; or mixtures thereof. Preferably the solvent used is toluene.

The process can be carried out at temperature range of about 30° C. to about 150° C. or reflux temperatures of the solvents used, preferably from about 100° C. to about 110° C.

The R-sitagliptin or its pharmaceutically acceptable salt thereof of the present invention may have less than 0.15% by weight of the corresponding (S)-enantiomer by chiral HPLC.

The present invention further provides R-sitagliptin dibenzyl-L-tartrate of formula II

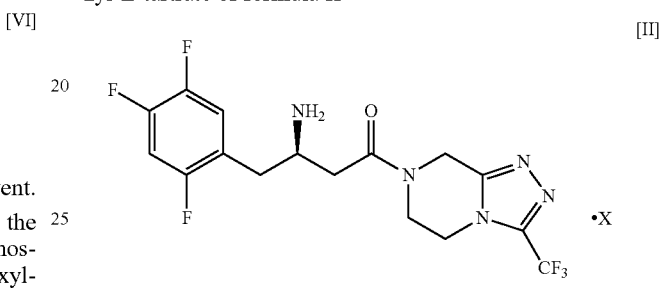

[II]

where X is dibenzyl-L-tartaric acid.

In yet another embodiment, the present invention provides a process for preparing sitagliptin phosphate of formula I, as shown in Scheme 1.

Scheme 1

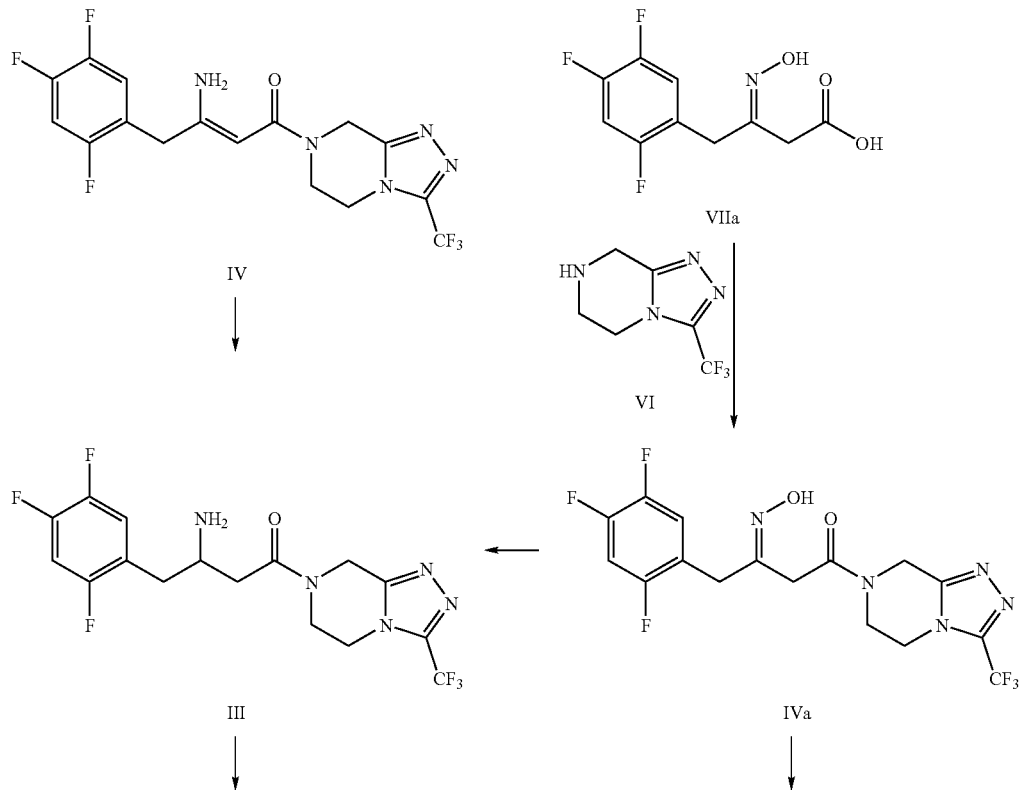

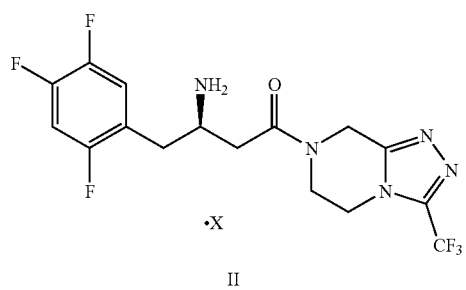

II

X = Chiral acid

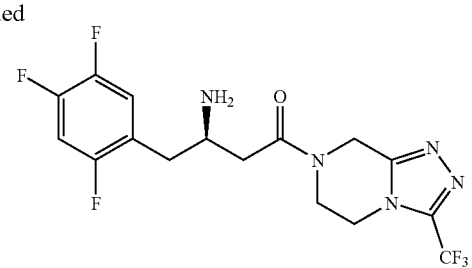

Ia

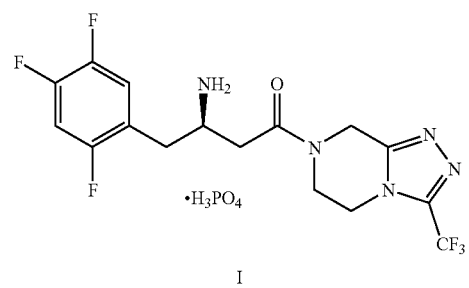

I

The compound of formula (IV) may be prepared according to the process disclosed in U.S. Pat. No. 7,326,708 which is incorporated herein by reference.

Suitably, one or more sequential steps are carried out without isolating intermediate compounds.

A further method for preparing optically substantially pure R-sitagliptin comprises:
a) resolving racemic sitagliptin by precipitation with a resolving acid in the presence of a solvent;
b) treating the recovered R-sitagliptin chiral acid salt with a base;
c) allowing the obtained R-sitagliptin racemate which is enriched in (R) enantiomer to mix with methanol,
d) removing the precipitate;
e) recovering from the mother liquid the optically substantially pure R-sitagliptin by crystallization.

The mother liquor from resolution step or the mother liquor from each recrystallisation, is enriched with (S)-sitagliptin. (S)-sitagliptin present in one or more of these liquors, or the pooled liquors, may be converted into racemic sitagliptin for reuse in a process according to the present invention substantially as hereinbefore described.

A further preferred aspect of a process according to the present invention comprises:
(a) resolving racemic sitagliptin with a chiral acid and obtaining a mother liquor enriched in (S)-sitagliptin;
(b) converting (S)-sitagliptin obtained from (a) to racemic sitagliptin; and
(c) if desired, employing racemic sitagliptin obtained from (b) in a process according to the present invention substantially as hereinbefore described.

Suitably, one or more mother liquors obtained from a process as described above, or pooled such mother liquors, may be treated with a base to remove any residual chiral acid and to thereby afford the free base enriched in (S)-sitagliptin. The free base can then be converted to the racemate, typically by reflux in a suitable solvent for several hours, optionally in the presence of a suitable acid for example HCl or a base for examples NaOH, which racemate can then be recycled for use in a process according to the present invention substantially as hereinbefore described.

The term "optically substantially pure" means here optical purity over about 90%, preferably over 95%, and more preferably over 99%, expressed as the percent enantiomeric excess. The terms "resolve" and "resolution" are intended to compass the complete or partial separation of the two optical enantiomers.

The crystalline diastereomeric salt can be filtered and the free base liberated by basifying the salt with e.g. potassium carbonate solution or ammonia. The mother liquid can be recovered after filtering and be further treated in order to recover the enantiomer which was not previously removed by precipitation. The treatment may comprise cooling the mother liquid and recovering the resulting crystalline diastereomeric salt.

R-sitagliptin dibenzyl-L-tartrate of formula II obtained by the process of present invention having an X-ray powder diffraction (XRPD) pattern with reflections at about: 6.5, 7.4, 10.9, 12.8, 14.9, 17.4, 17.9, 19.2, 21.5, 22.4, and 23.7±0.2 degrees 2 theta.

The R-sitagliptin dibenzyl-L-tartrate of formula II obtained by the process of present invention may have an XRPD pattern which is substantially in accordance with FIG. 1.

R-sitagliptin dibenzyl-L-tartrate of formula II obtained by the process of the present invention is further characterized by differential scanning calorimetry (DSC) having thermogram with sharp endotherm at about 176.73° C. with onset at about 171.49° C. and endset at about 176.73° C.

Figure 2:
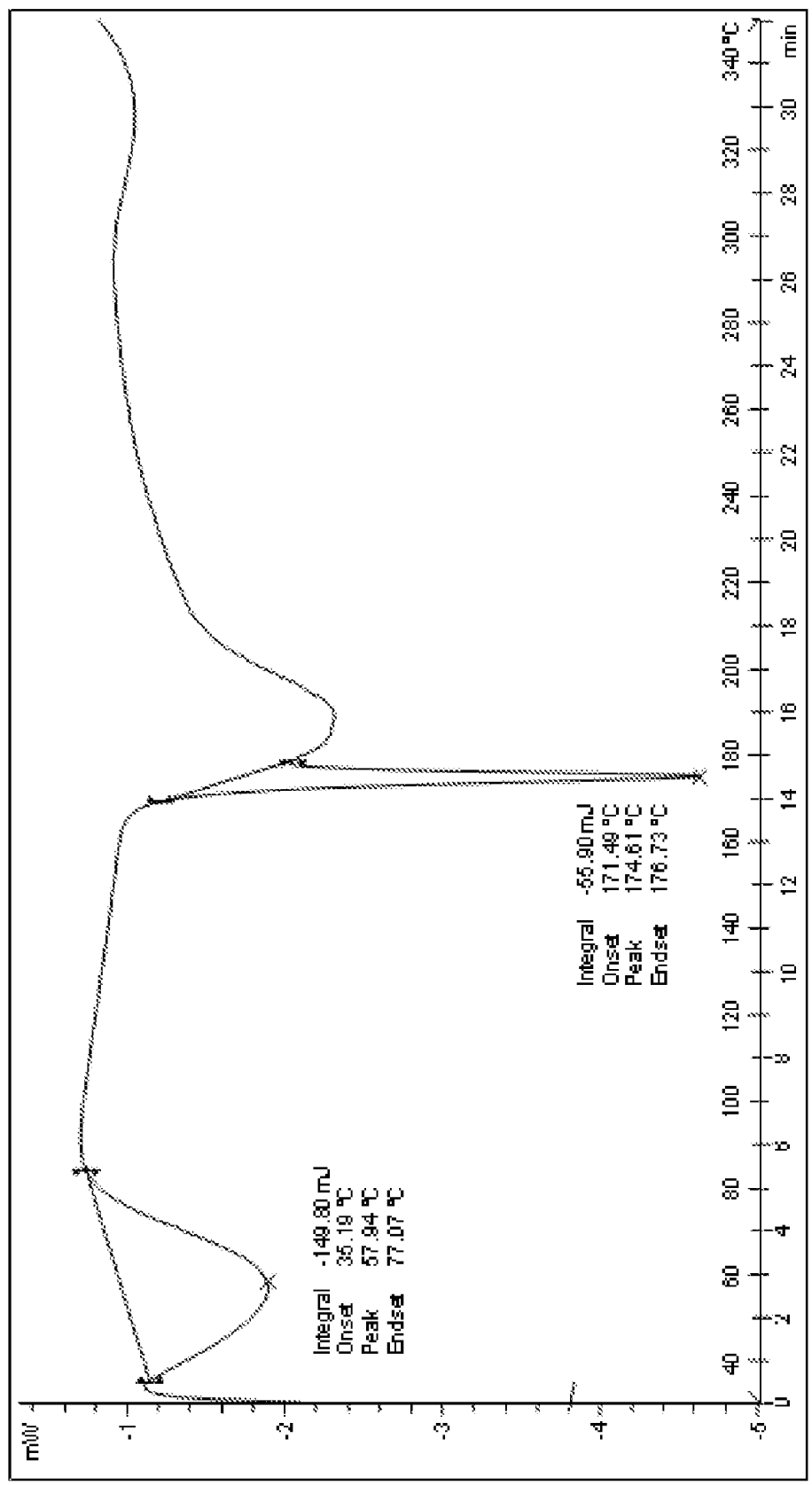
FIG. 2: Shows a Differential scanning calorimetry (DSC) of R-sitagliptin dibenzyl-L-tartrate of Formula II as prepared by example 5c.

The R-sitagliptin dibenzyl-L-tartrate of formula II obtained by the process of present invention may have a DSC thermogram which is substantially in accordance with FIG. 2.

R-sitagliptin of formula Ia obtained by the process of present invention having an X-ray powder diffraction (XRPD) pattern with reflections at about: 7.3, 17.6, 18.8, 21.2, 21.5, 22.4, 24.1, 24.4, 24.7, 27.0, and 28.7±0.2 degrees 2 theta. X-ray powder diffraction measurements were performed on a Philips X'pert PRO Diffractometer using Cu Kα radiation (Cu Kα1=1.54060 Å). The X-ray source is operated at 45 kV and 40 mA. Spectra are recorded at start angle from 2° to 50° 2θ, a step size 0.0167° with a time per steps of 50 seconds.

Figure 3:
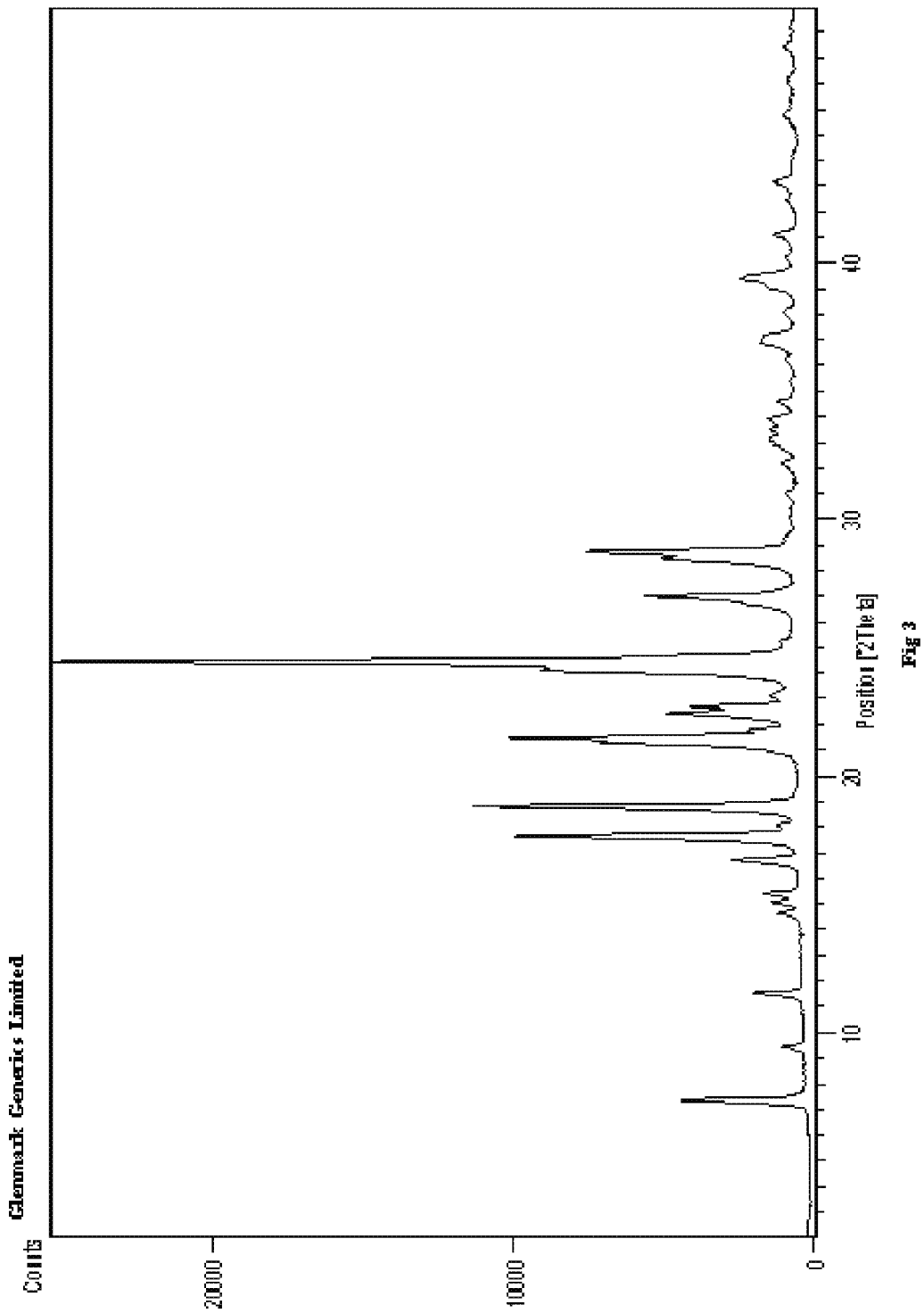
FIG. 3: Shows a powder X-ray diffraction pattern of R-sitagliptin of Formula Ia as prepared by example 6.

The R-sitagliptin of formula Ia obtained by the process of present invention may have an XRPD which is substantially in accordance with FIG. 3.

R-sitagliptin of formula Ia obtained by the process of present invention is further characterized by differential scanning calorimetry (DSC) having thermogram with sharp endotherm at about 117.66° C. with onset at about 116.37° C. and endset at about 119.58° C.

Figure 4:
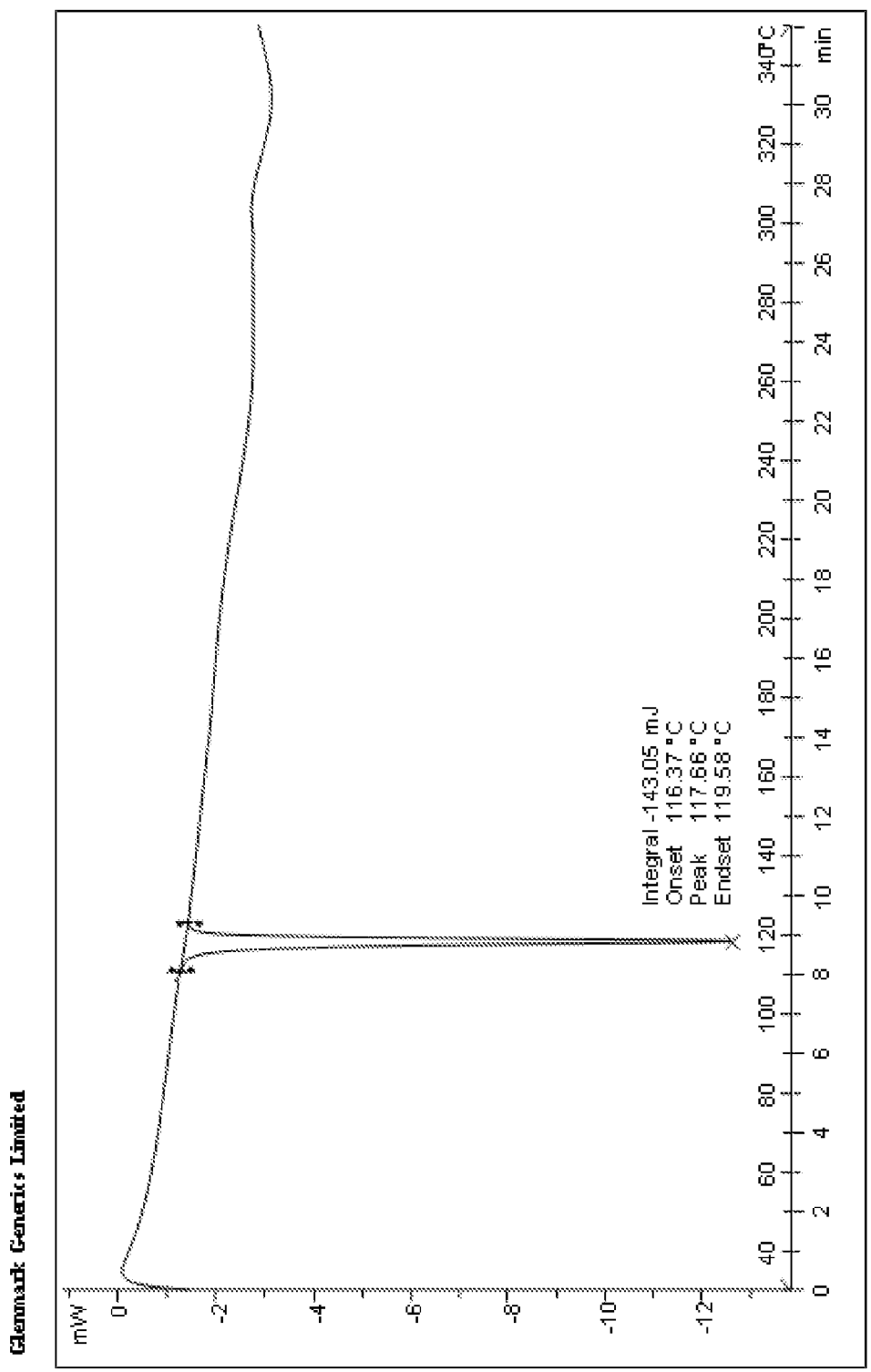
FIG. 4: Shows a Differential scanning calorimetry (DSC) of R-sitagliptin of Formula Ia as prepared by example 6.

The R-sitagliptin of formula Ia obtained by the process of present invention may have a DSC thermogram which is substantially in accordance with FIG. 4.

The DSC thermogram is recorded by following the procedure: Take the empty aluminum standard 40 µL pan and put it in the microbalance. Take and weigh approximately below 2.0 mg of sample. Slightly pierce the cover of the pan and seal it. Place the sample pan in the left position on mark "S" and empty reference pan in the right position on mark "R" of the blue DSC sensor. Place the furnace lid, and maintain the nitrogen gas as purge gas. Select the method temperature range is 30° C. to 350° C. and heating rate is 10° C./Minute. Under these conditions run the sample.

Typically the product obtained by the above described method contains about 90 wt % of the desired enantiomer of (Ia). The purity of the product can be increased to about 96 wt % by recrystallization. Methanol is the preferred recrystallization solvent. For example, the product which is enriched in (−) enantiomer is recrystallized by adding the product to methanol solvent, refluxing the mixture and filtering precipitate. The filtrate is concentrated, if necessary, and cooled in order to crystallize the (R)-enantiomer of (Ia). This allows recovering the substantially pure (−) enantiomer of (I) from the mother solution by crystallization.

The precipitation is carried out with cooling, decreasing the amount of the solvent and/or by adding a contrasolvent The free base obtained may be optionally purified by recrystallization or slurrying in suitable solvents.

Recrystallization involves providing a solution of crude R-sitagliptin in a suitable solvent and then crystallizing the solid from the solution.

Suitable solvents in which R-sitagliptin can be dissolved for purification include but are not limited to: $C_1$-$C_5$ ketones such as acetone, ethyl methyl ketone, butanone and the like; alcohols such as ethanol, methanol, and isopropanol; ethers such as such as tetrahydrofuran, 1,4-dioxane, ethyl acetate and the like; water; and mixtures thereof.

The concentration of the R-sitagliptin in a solvent or mixture of solvents can range from about 40% to about 80% or more. The solution can be prepared at an elevated temperature if desired to achieve a higher solute concentration. Any temperature is acceptable for the dissolution as long as a clear solution of the R-sitagliptin is obtained and is not detrimental to the drug substance chemically or physically. The solution may be brought down to a lower temperature for further processing if required or an elevated temperature may be used. A higher temperature for dissolution will allow the precipitation from solutions with higher concentrations of R-sitagliptin, resulting in better economies of manufacture.

The product may optionally be further dried. Drying can be suitably carried out in a tray dryer, vacuum oven, air oven, fluidized bed drier, spin flash dryer, flash dryer and the like. The drying can be carried out at temperatures of about 35° C. to about 70° C. The drying can be carried out for any desired time periods to achieve the desired product purity, times from about 1 to 20 hours frequently being adequate.

R-sitagliptin prepared by above methods can also be converted into its pharmaceutically acceptable salts such as phosphate, hydrochloride, and the like; preferably phosphate.

The process briefly involves the reacting a pharmaceutically acceptable acid with R-sitagliptin in solution.

Suitable pharmaceutically acceptable acids which can be used include, but are not limited to: inorganic acids such as phosphoric acid, hydrochloric acid, hydrobromic acid, hydroiodic acid; and organic acids such as acetic acid, tartaric acid, oxalic acid, and the like. Preferably phosphoric acid.

Optionally, the acid is dissolved in a solvent before adding it to the solution of R-sitagliptin free base.

The solvent used for the dissolution of R-sitagliptin and the acid may be the same, or different solvents may be used.

Optionally, the acid addition salt obtained can be purified further by recrystallization or slurrying in suitable solvents.

Suitable solvents in which the acid addition salt of R-sitagliptin can be dissolved for purification include but are not limited to: $C_1$-$C_5$ ketones such as acetone, ethyl methyl ketone, butanone and the like; alcohols such as ethanol, methanol, and isopropanol; ethers such as tetrahydrofuran, 1,4-dioxane, ethyl acetate and the like; water; and mixtures thereof.

The product may optionally be further dried. Drying can be suitably carried out in a tray dryer, vacuum oven, air oven, fluidized bed drier, spin flash dryer, flash dryer and the like. The drying can be carried out at temperatures of about 35° C. to about 90° C. The drying can be carried out for any desired time until the required product purity is achieved, time periods from about 1 to 20 hours frequently being sufficient.

R-sitagliptin or any of the pharmaceutically acceptable salts of R-sitagliptin prepared in accordance with the present invention contains less than about 0.5%, of the corresponding impurities as characterized by a chiral HPLC (high performance liquid chromatography) chromatogram obtained from a mixture comprising the desired compound and one or more of the said impurities, preferably less than about 0.1%. The percentage here refers to weight percent obtained from the area-% of the peaks representing the impurities. R-sitagliptin and salts thereof also are substantially free of other process-related impurities The process of the present invention advantageously provides R-sitagliptin or its pharmaceutically acceptable salts in relatively high purity, e.g., greater than about 98% ee and preferably greater than about 99%.

The R-sitagliptin or its pharmaceutically acceptable salts obtained by the processes of the present invention has residual organic solvent less than the amount recommended for pharmaceutical products, as set forth for example in ICH guidelines and U.S. Pharmacopoeia; the recommended amount is less than 5000 ppm for methanol, ethyl acetate and acetone; less than 800 ppm for toluene, dichloromethane, dimethyl formamide and diisopropyl ether. Preferably, the amount is less than about 5000 ppm residual organic solvent, preferably, more preferably less than about 2000 ppm residual organic solvent, most preferably, less than about 700 ppm.

The pharmaceutical composition comprising R-sitagliptin or its pharmaceutically acceptable salts prepared by the processes of present invention may be formulated for oral administration. Accordingly, $D_{90}$ particle size of the unformulated sitagliptin or pharmaceutically acceptable salts thereof used as starting material in preparing a pharmaceutical composition generally is less than 300 microns, preferably less than about 200 microns, more preferably less than 100 microns, still more preferably less than about 50 microns and still more preferably less than about 20 microns.

Any milling, grinding micronizing or other particle size reduction method known in the art can be used to bring the solid state sitagliptin or its pharmaceutically acceptable salt thereof into any desired particle size range as set forth above.

Another aspect of the present invention is directed to a pharmaceutical dosage form containing sitagliptin or its pharmaceutically acceptable salts thereof. The pharmaceutical dosage may be in any form, for example, compacted tablets, powder suspensions, capsules, and the like. The compositions of the present invention can be administered to humans and animals in such dosage forms as oral, rectal, parenteral (intravenous, intramuscular, or subcutaneous), intracisternal, intravaginal, intraperitoneal, local (powders, ointments or drops), ophthalmic, transdermal, or sublingual forms or as a buccal or nasal spray. Oral dosage forms include, but are not limited to, pills, capsules, troches, sachets, suspensions, powders, lozenges, elixirs, tablets, capsules (including soft gel capsules), ovules, solutions, and the like which may contain flavoring or coloring agents, for immediate-, delayed-, modified-, or controlled-release such as sustained-, dual-, or pulsatile delivery applications. R-sitagliptin or its pharmaceutically acceptable salt thereof prepared by the process as described herein also may be administered as suppositories, ophthalmic ointments and suspensions, and parenteral suspensions, which are administered by other routes. The most preferred route of administration of the sitagliptin or its pharmaceutically acceptable salts thereof of the present invention is oral.

The active ingredient of the invention may also be administered via fast dispersing or fast dissolving dosage forms or in the form of high energy dispersion or as coated particles. Suitable pharmaceutical composition of the invention may be in coated or uncoated form as desired.

Tableting compositions may have few or many components depending upon the tableting method used, the release rate desired and other factors. For example, the compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols like mannitol and sorbitol, acrylate polymers and copolymers, as well as pectin, dextrin and gelatin.

Other excipients contemplated by the present invention include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

Capsule dosages will contain the solid composition within a capsule which may be coated with gelatin. Tablets and powders may also be coated with an enteric coating. The enteric-coated powder forms may have coatings comprising phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric coating.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Example 1

PREPARATION OF 5-[1-HYDROXY-2-(2,4,5 TRIFLUOROPHENYL)ETHYLIDENE]-2,2-DIMETHYL-1,3-DIOXANE-4,6-DIONE 200 gm of 2,4,5-trifluorophenyl acetic acid, 108 ml of oxalic acid, 10 ml of dimethyl formamide and 2000 ml of methylenedichloride were charged into a clean and dry round bottom flask followed by stifling at about 25-30° C. for about 2-3 hours., the progress of the reaction was monitored by thin layer chromatography (TLC) including high performance liquid chromatography (HPLC), after the completion of the reaction, the reaction mass was cooled to about −5° C. Prereacted solution of 280 gm of 4-dimethylamino pyridine and 226 gm of 2,2-dimethyl-1,3-dioxane-4,6-dione in 1000 ml of methylenedichloride was added to the reaction mass between the temperature of about −5~0° C. and maintained the reaction mixture at the same temperature until the completion of reaction, which was monitored by TLC or HPLC. 300 gm of dried product of 5-[1-hydroxy-2-(2,4,5-trifluorophenyl)ethylidene]-2,2-dimethyl-1,3-dioxane-4,6-dione (Formula VII) was obtained by the acidic aqueous workup followed by solid precipitation with diisopropyl ether. The isolated compound has been characterized by Melting points, Mass $^1$H NMR and HPLC purity.

| | |
|---|---|
| Mass | 315.31 [M − H]$^−$ |
| $^1$H NMR (300 MHz, CDCl3) | 7.1, 6.9 (2H, m), 4.43 (2H, s), 1.7 (6H, s) |
| Melting point | [86.44-109.5] ° C. |
| HPLC purity | NLT = 98%. |

Example 2

PREPARATION OF 4-OXO-4-[3-(TRIFLUOROMETHYL)-5,6-DIHYDRO[1,2,4]TRIAZOLO[4,3-a]PYRAZIN-7(8H)—YL]-1-(2,4,5-TRIFLUOROPHENYL)BUTAN-2-ONE 547 gm of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (Formula V) was obtained by adding 500 gm of 5-[1-hydroxy-2-(2,4,5-trifluorophenyl)ethylidene]-2,2-dimethyl-1,3-dioxane-4,6-dione in to the solution 5000 ml toluene containing 440 gm of 3-(trifluoromethyl)-5,6,7,8-tetrahydro[1,2,4]triazolo[4,3-a]pyrazine.hydrochloride (Formula VI) and 1100 ml of diisopropyl ethylamine at about 25-30° C. followed by heating the reaction mass to toluene reflux temperature until the completion of the reaction, as monitored by TLC or HPLC. The isolation of the above said product was done by ethylacetate and aqueous—acidic workup followed by distillation.

The isolated compound has been characterized by Mass and HPLC purity.

| | |
|---|---|
| Mass | 407.18 [M + H]+ |
| HPLC purity | NLT = 85%. |

Example 3

PREPARATION OF 4-OXO-4-[3-(TRIFLUOROMETHYL)-5,6-DIHYDRO[1,2,4]TRIAZOLO[4,3-a]PYRAZIN-7(8H)—YL]-1-(2,4,5-TRIFLUORO PHENYL)BUT-2-EN-2-AMINE 540 gm of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one dissolved in 5400 ml of methanol and cooled to 0-5° C. 540 gm of ammonium acetate and 1080 ml of aqueous ammonia (25w/w) solution was added and maintained for about 15-30 minutes at about 40-45° C. until the completion of the reaction, as monitored by TLC or HPLC. 387 gm of 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (Formula IV) was obtained by filtration and drying. The isolated compound has been characterized by Melting Points, Mass $^1$H NMR and HPLC purity.

| | |
|---|---|
| Mass | 406.74 [M + H]+ |
| $^1$H-NMR (400 MHz, DMSO) | 7.5 (2H, m), 4.86 (1H, s), 4.82 (1H, s), 4.1 (4H, m), 3.8 (2H, m), 3.4 (1H, s), 3.32 (1H, s). |
| Melting point | 193.77° C. |
| HPLC purity | NLT = 95%. |

Example 4

4-OXO-4-[3-(TRIFLUOROMETHYL)-5,6-DIHYDRO [1,2,4]TRIAZOLO[4,3-A]PYRAZIN-7(8H)—YL]-1-(2,4,5-TRIFLUOROPHENYL) BUTAN-2-AMINE 50 gm of 4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine with 150 ml of methanol and 350 ml of methylenedichloride with 19 gm of sodiumcyano borohydride in the presence of 30 ml of acetic acid with the temperature range of about −5° C. to about 25-30° C. under nitrogen atmosphere. 46 gm of 4-Oxo-4-[3-(trifluoromethyl)-5,6-dihydro[1,2,4]triazolo[4,3-a]pyrazin-7(8H)-yl]-1-(2,4,5-trifluorophenyl)butan-2-amine (Formula III) was isolated by aqueous ammonia work-up.

| | |
|---|---|
| HPLC purity | NLT = 85%. | b) 4-OXO-4-[3-(TRIFLUOROMETHYL)-5,6-DIHYDRO[1,2,4]TRIAZOLO[4,3-a]PYRAZIN-7(8H)—YL]-1-(2,4,5-TRIFLUOROPHENYL)BUTAN-2-AMINE 3.5 gm of 4-Oxo-4-[3-(trifluoromethyl)-5,6-dihydro[1,2,4]triazolo[4,3-a]pyrazin-7(8H)-yl]-1-(2,4,5-trifluorophenyl)butan-2-amine isolated as solid from 9.2 gm of crude with 117 ml of toluene crystallization with the temperature range from about 70-75° C. to about 25-30° C. The isolated compound has been characterized by Melting points, Mass $^1$H NMR and HPLC purity.

| | |
|---|---|
| Mass | 408.43 [M + H]+ |
| $^1$H-NMR (300 MHz, CDCl3) | 7.0 (H, m), 6.9 (1H, m), 4.9 (2H, m, s), 4.1 (4H, m), 3.6 (1H, s), 3.5 (1H, bs) 2.8–2.4 (4H, bm), 1.7 (2H, bs) |
| Melting point | 97.03° C. |
| HPLC purity | NLT = 95%. |

Example 5

(2R/2S)-4-OXO-4-[3-(TRIFLUOROMETHYL)-5,6-DIHYDRO [1,2,4]TRIAZOLO[4,3-a]PYRAZIN-7(8H)—YL]-1-(2,4,5-TRIFLUOROPHENYL)BUTAN2-AMINE(−)DBLTA SALT a) 41 gm of (2R/2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine dissolved in 250 ml of acetone at 25-30° C. was added to the solution of 35 gm of (−) Dibenzolyl-L-Tartaric acid dissolved in 1000 ml of diisopropyl ether at 25-30° C. for 15-30 minutes followed by stirring the reaction mass to 2 hours. 61 gm of (R/S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine. (−) DBLTA diastereomeric salt (Formula II) was obtained by filtration and followed by drying the solid at 50-55° C. for 12 hours. The isolated solid has been characterized by chiral HPLC, XRD and DSC.

Chiral HPLC purity was 50:50(S/R diastereoisomer ratio).

b) PURIFICATIONS OF (2S/2R)-4-OXO-4-[3-(TRIFLUOROMETHYL)-5,6-DIHYDRO[1,2,4]TRIAZOLO[4,3-A]PYRAZIN-7(8H)—YL]-1-(2,4,5-TRIFLUORO PHENYL) BUTAN-2-AMINE (−) DBLTA DIASTREOMERIC SALT 5 gm of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine(−)DBLTA diastereomeric salt was obtained by repeated reflux-leaching with methanol at 65° C. to 25-30° C. followed by two recrystallisations with 300 ml and 250 ml of methanol at the temperature of 65° C. to 25-30° C. The isolated solid has been characterized by chiral HPLC, XRD and DSC. Chiral HPLC 95.42% was observed.

c) PREPARATION CUM PURIFICATION OF (2R)-4-OXO-4-[3-(TRIFLUOROMETHYL)-5,6-DIHYDRO[1,2,4]TRIAZOLO[4,3-A]PYRAZIN-7(8H)—YL]-1-(2,4,5-TRIFLUOROPHENYL)BUTAN-2-AMINE(−)DBLTA 212 gm of (2R/2S)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine dissolved in 848 ml of methanol was added to the solution of 172 gm of (−) dibenzolyl-L-tartaric acid dissolved in 848 ml of methanol at reflux temperature for about 15-30 minutes followed by stifling the reaction mass for about 2 hours at about 65-70° C. 252 gm of white solid was isolated by filtration at about 25-30° C. About 65-70% chiral purity was observed.

The purity was further enhanced by recrystallisation with methanol-water system at 65-70° C. with volume of 25 to 35 of (2R/2S)-4-oxo-4-[3-(trifluoromethyl)-5,6-dihydro[1,2,4]triazolo[4,3-a]pyrazin-7 (8H)-yl]-1-(2,4,5-trifluorophenyl)butan-2-amine (Formula II) for twice, 106 gm of white solid was isolated by filtration. The isolated solid been characterized by chiral HPLC, XRD and DSC The chiral purity observed was 85~90%.

Example-6

PREPARATION OF (2R)-4-OXO-4-[3-(TRIFLUOROMETHYL)-5,6-DIHYDRO[1,2,4]TRIAZOLO[4,3-a]PYRAZIN-7(8H)—YL]-1-(2,4,5-TRIFLUOROPHENYL)BUTAN-2-AMINE 105 gm of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine(−)dibenzyl-L-tartaric acid was suspended in 525 ml of methylene dichloride and 525 ml of water. The pH of the suspension was adjusted to about 11 to 12 by addition of 10% aqueous sodium hydroxide solution over about 15-20 minutes under stirring. Organic and aqueous layers were separated and the organic layer was distilled completely at about 30-35° C. under vacuum. The solid separated (Formula Ia) was isolated by toluene crystallization and was dried at about 55-60° C. for 12 hours to afford 33.5 gm of the title compound.

Purity by HPLC: 99.36%.
Purity by Chiral HPLC: 99.7%. Melting point: 117.66° C.

Example-7

PREPARATION OF (2R)-4-OXO-4-[3-(TRIFLUOROMETHYL)-5,6-DIHYDRO[1,2,4]TRIAZOLO-[4,3-a]PYRAZIN-7(8H)—YL]-1-(2,4,5-TRIFLUORO PHENYL) BUTAN-2-AMINE DIHYDROGEN PHOSPHATE 5 gm of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine and 150 ml of ethanol were charged into a clean and dry round bottom flask followed by heating to about 50-55° C. 1.26 ml of 85% v/v of phosphoric acid was added to the above solution at about 50-55° C. in one lot. The reaction mixture was maintained under stifling at about 75-78° C. for about 30 minutes. The separated solid (Formula I) was filtered and the solid obtained was dried at about 50-55° C. for about 12 hours to afford 4 gm of the title compound.

Specific optical rotation [SOR]: −20 to −22 [C=1% water)
Melting point: 212° C. to 213.5° C.
Purity by Chiral HPLC: 99.92%; Purity by HPLC: 99.95%.

We claim:
1. Crystalline (R)-sitagliptin having an x-ray powder diffraction pattern comprising reflections at 7.3°, 17.6°, 18.8°, 21.2°, 21.5°, 22.4°, 24.1°, 24.4°, 24.7°, 27.0° and 28.7° ±0.2° 2θ.
2. The crystalline (R)-sitagliptin of claim 1, having a differential scanning calorimetry thermogram with an endotherm at 117.66° C. with an onset at 116.37° C. and an endset at 119.58° C.

* * * * *